United States Patent [19]

Murray et al.

[11] Patent Number: 5,792,877

[45] Date of Patent: Aug. 11, 1998

[54] GIRARD DERIVATIVES OF TAXANES

[75] Inventors: Christopher K. Murray; Jeffrey T. Beckvermit; Dominick J. Anziano, all of Boulder, Colo.

[73] Assignee: Hauser Chemical Research, Inc., Boulder, Colo.

[21] Appl. No.: 743,325

[22] Filed: Nov. 4, 1996

Related U.S. Application Data

[60] Continuation of Ser. No. 331,682, Oct. 31, 1994, abandoned, which is a division of Ser. No. 224,758, Apr. 8, 1994, Pat. No. 5,364,947, which is a continuation-in-part of Ser. No. 120,170, Sep. 10, 1993, Pat. No. 5,334,732, which is a continuation-in-part of Ser. No. 909,080, Jul. 2, 1992, abandoned.

[51] Int. Cl.⁶ .................. C07D 305/00; C07D 307/02
[52] U.S. Cl. ............................ 549/510; 549/500
[58] Field of Search ........................ 549/510, 500

[56] References Cited

PUBLICATIONS

"Approaches to the Synthesis of Modified Taxols", Jitrangsri dissertation, Aug., 1986.

*Primary Examiner*—Leon B. Lankford, Jr.
*Attorney, Agent, or Firm*—Dean P. Edmundson

[57] ABSTRACT

A process for separating non-oxidizable compounds from a mixture containing at least one oxidizable compound. The mixture is contacted with ozone to oxidize oxidizable compounds to form oxidized compounds which are then converted to water-soluble hydrazones, followed by separation of the hydrazones from the mixture using precipitation, liquid/liquid extraction, chromatography, etc.

4 Claims, 10 Drawing Sheets

Figure 2

1 taxol   R = C₆H₅CO
2 cephalomannine   R = CH₃CH=CCO
                              |
                              CH₃

Cephalomannine $+$

Taxol $\downarrow O_3$

Ozo-Cephalomannine $+$

Taxol $\downarrow$ Girard hydrazide/AcOH

Ozo-Cephalomannine-Girard Hydrazone

$+$

Taxol

$\downarrow$ Separation

Ozo-Cephalomannine-Girard hydrazone          Taxol

Figure 6

Girard T hydrazide

Girard P hydrazide general hydrazide x = water soluble functional group general hydrazine x = water soluble functional group

GIRARD DERIVATIVES OF TAXANES

CROSS-REFERENCE TO RELATED APPLICATION

This is a continuation of application Ser. No. 08/331,682 filed on Oct. 31, 1994 now abandoned, which is a divisional of application Ser. No. 08/224,758 filed on Apr. 8, 1994 now U.S. Pat. No. 5,364,947, which is a continuation-in-part of U.S. patent application Ser. No. 08/120,170, filed Sep. 10, 1993, now U.S. Pat. No. 5,334,732 which is a continuation-in-part of U.S. patent application Ser. No. 07/909,080, filed Jul. 2, 1992 now abandoned.

BACKGROUND OF THE INVENTION

1. Field of the Invention

This invention relates to a process by which ozone oxidizable compounds are separated from non-oxidizable compounds in biomass extracts. More particularly, this invention relates to the separation of cephalomannine and related ozone oxidizable compounds from taxol and other non-oxidizable taxanes in extracts of biomass containing a complex mixture of compounds.

2. Description of the State of Art

Between the years 1958 and 1980, extracts of over 35,000 plant species were tested for anticancer activity as part of an NCI-sponsored program Chemists Monroe E. Wall and M. C. Wani first isolated a crude extract concentrate from yew tree (*Taxus brevifolia*) bark and wood samples in 1963. Initial screening showed the extract to be a potential anticancer agent, being very active against an unusually wide range of rodent cancers. Isolation of the active agent in the crude extract took several years due to the very low concentrations of the agent present in the plants and due to the difficulty of separating the closely-related diterpenoids. The active agent was identified, the structure determined and the compound was named taxol, in 1971. Despite taxol's excellent activity in model tumor systems, clinical trials were delayed owing to short supplies of the drug and formulation problems related to the drug's low solubility.

In ongoing clinical trials, taxol has shown promising results in fighting advanced cases of ovarian, breast and other cancers. Recently, taxol was approved by the Food and Drug Administration for the treatment of refractory ovarian cancer; however, taxol is extracted in limited quantities from a natural vegetation that is in short supply.

Figure 2:
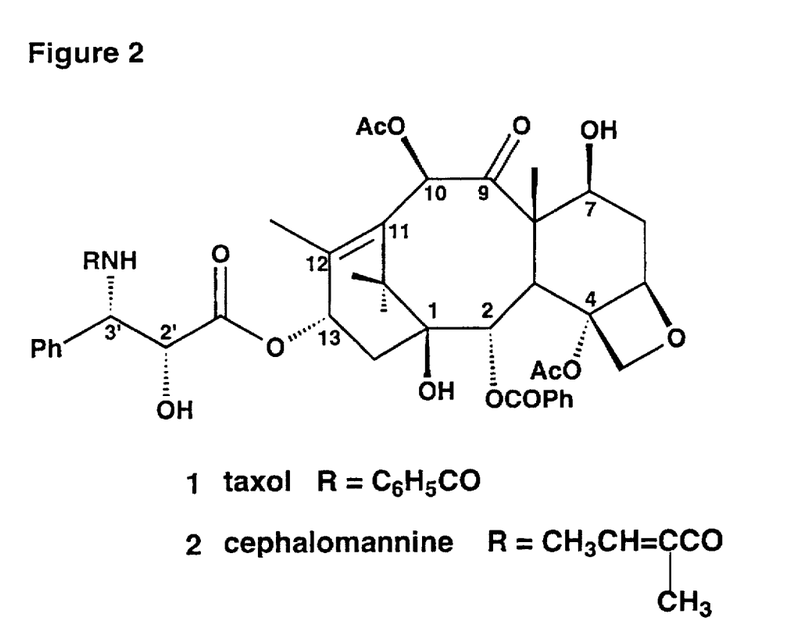
FIG. 2 compares the structure of taxol and cephalomannine.

Currently, taxol is isolated on a large scale only from the bark of *Taxus brevifolia*. However, taxol can be potentially isolated on a large commercial scale from other parts of Taxus and also from cell cultures of Taxus. See U.S. Pat. No. 5,019,504, issued to Christen et al. The method of isolation of taxol from any natural source is complex. A particularly difficult and expensive part of the isolation of taxol is the separation of the closely-related diterpenoid cephalomannine. The only structural difference between taxol and cephalomannine, as shown in structures 1 and 2 of FIG. 2, respectively, involves the side chain portion of the compound, thus giving rise to similar chemical properties. Achieving a clean separation of these closely related compounds is extremely difficult, but can be accomplished by various means of chromatography. However, the use of chromatography on a commercial scale is an extremely expensive step in the process of separating compounds and would be ultimately reflected in the cost of the drug.

Figure 3:
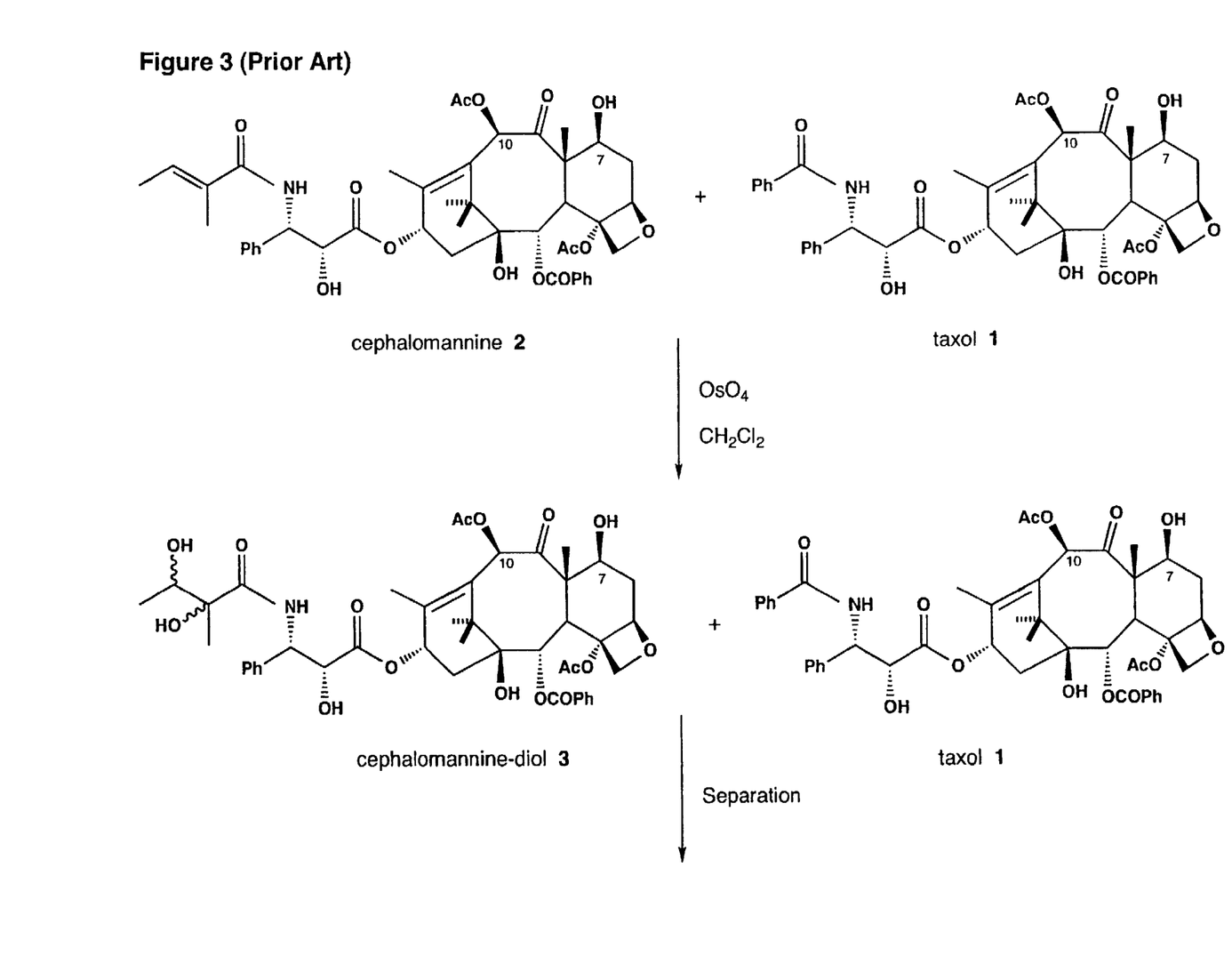
FIG. 3 shows the reaction of cephalomannine with osmium tetroxide in the presence of taxol.
Figure 4:
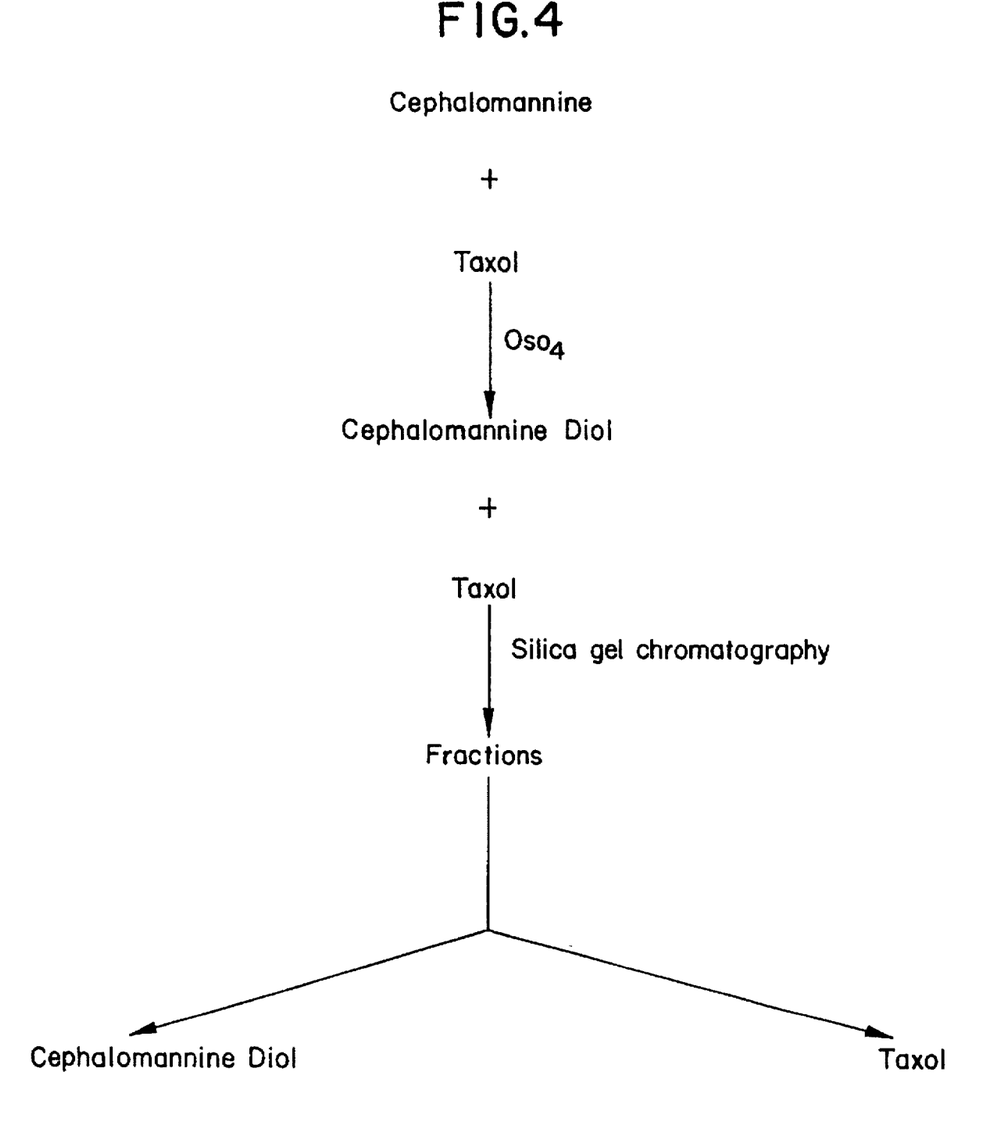
FIG. 4 shows a flow diagram for the separation of taxol and cephalomannine using osmium tetroxide and silica gel chromatography.

There have been some methods developed for improving the separation of taxol from cephalomannine; however, chromatography is still required for a complete separation of the two compounds. For example, Kingston et al. reported a method, under stoichiometric or catalytic conditions, to modify the side chain of cephalomannine in the presence of taxol in purified and/or partially-purified taxane mixtures. See, Kingston et al. Journal of Organic Chemistry, 55 (2): 259–261 (1992), incorporated herein by reference. In the partially-purified mixture, disclosed by Kingston et al., taxol and cephalomannine were present in a total amount of about 80% by weight. Selective oxidation of the tiglate group of cephalomannine using osmium tetroxide under stoichiometric or catalytic conditions yielded a diol, shown in FIG. 3 as structure 3, and did not affect the structure of taxol. The diol was separated from the reaction mixture by silica gel chromatography as shown in FIGS. 3 and 4.

The above technical paper by Kingston et al. discloses a process whereby the chemical properties of cephalomannine are altered thus allowing for a cleaner separation of taxol from the newly formed diol; however, as explained in further detail below, the Kingston et al. process is not suitable for use with unpurified taxane mixtures. A very long reaction time is required for the complete oxidation of cephalomannine by osmium tetroxide. Furthermore, the very high ratio of osmium tetroxide to cephalomannine results in a two-fold disadvantage. First, the reagent osmium tetroxide is very expensive, i.e., $76.00 per gram from one common commercial supplier in 1993. Second, due to the extreme toxicity of osmium tetroxide, careful handling is required for both the reagent and the resulting waste associated with the process.

There is still a need, therefore, for an inexpensive, simple, safe and effective separation of cephalomannine from taxol at a wide range of purities.

SUMMARY OF THE PRESENT INVENTION

Accordingly, it is an object of the present invention to provide a method for separating ozone oxidizable compounds from non-oxidizable compounds.

Another object of this invention is to provide a method for separating cephalomannine and related compounds from taxol and other unreactive compounds.

A further object of the present invention is to provide a method for chemically modifying cephalomannine in the presence of taxol in such a manner that no appreciable amount of taxol is modified.

As used herein, the term "other unreactive compounds" includes taxanes and compounds that are not easily oxidized by ozone in the process of the present invention, and are not reactive to hydrazides or hydrazines in the process of the present invention.

As used herein, the term "related compounds" in regards to the process of the present invention, includes taxanes and other compounds that contain easily ozone oxidizable olefin functional groups, such as, an olefin group that is not substituted on one end of the double bond. In addition, functional groups such as primary and secondary alcohols may also be oxidized to ketones and aldehydes. Olefins that are potentially reactive in the process of the present invention include those with four bulky substituents, see FIG. 2, carbons 11 and 12, for an example.

As used herein, the term "reactive carbonyl compounds" includes ketones and aldehydes that are reactive to hydrazides and hydrazines in the process of the present invention. By definition, reactive carbonyl compounds will be separated from taxol and other unreactive taxanes in mixtures whether or not oxidized cephalomannine is present in the mixture.

Additional objects, advantages and novel features of this invention shall be set forth in part in the description and Examples that follow, and in part will become apparent to those skilled in the art upon examination of the following specification or may be learned by the practice of this invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein, the method of this invention comprises contacting a biomass extract having a mixture of oxidizable and non-oxidizable compounds with an oxidizing reagent and then converting the resulting oxidized compounds to water-soluble hydrazones which can easily be separated from compounds that are not readily oxidizable based on differing solubilities and polarities.

BRIEF DESCRIPTION OF THE DRAWINGS

The accompanying drawings, which are incorporated in and form a part of the specifications, illustrate the preferred embodiments of the present invention, and together with the description serves to explain the principles of the invention.

DETAILED DESCRIPTION OF THE INVENTION

Figure 1:
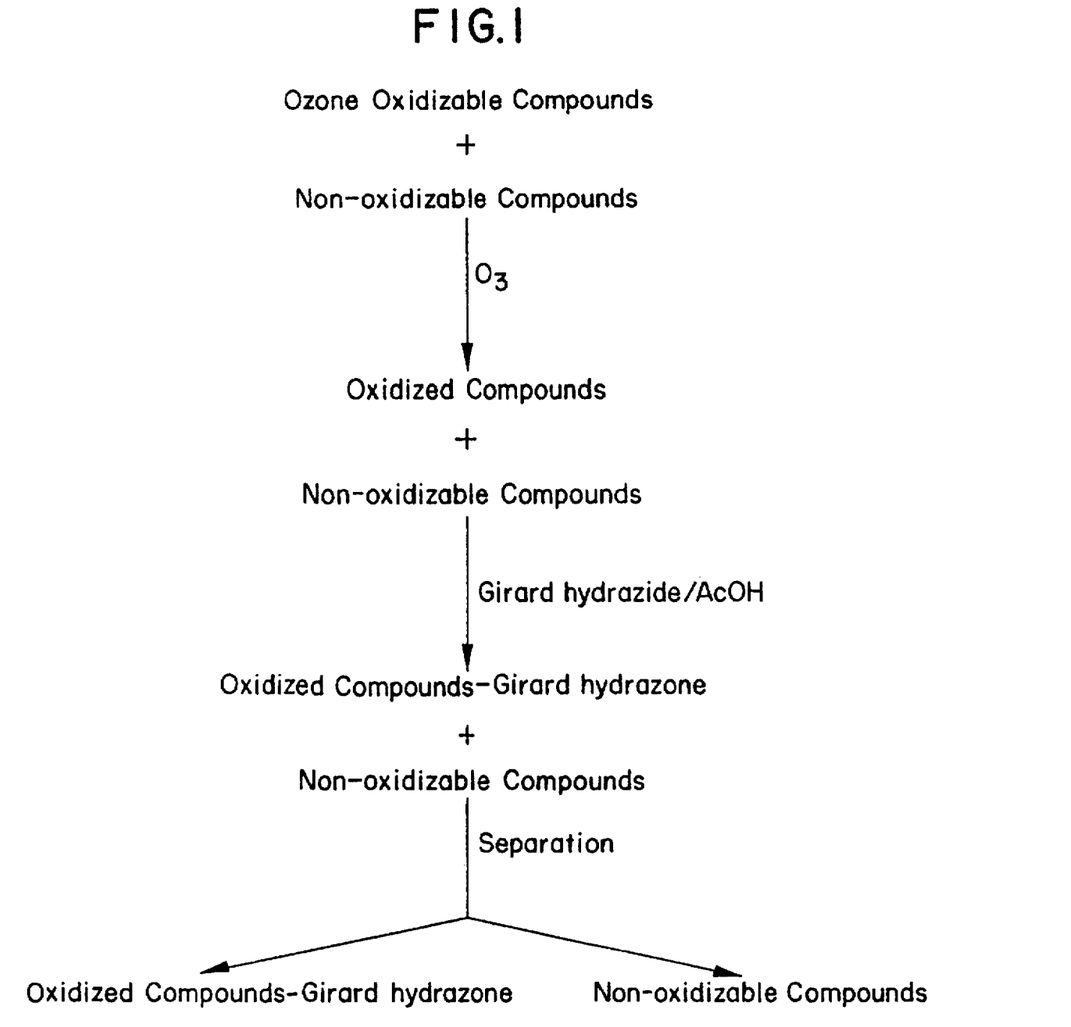
FIG. 1 shows a flow diagram for the separation of ozone oxidizable compounds and non-oxidizable compounds using ozone, followed by treatment with Girard hydrazide and a separation method.
Figure 5:
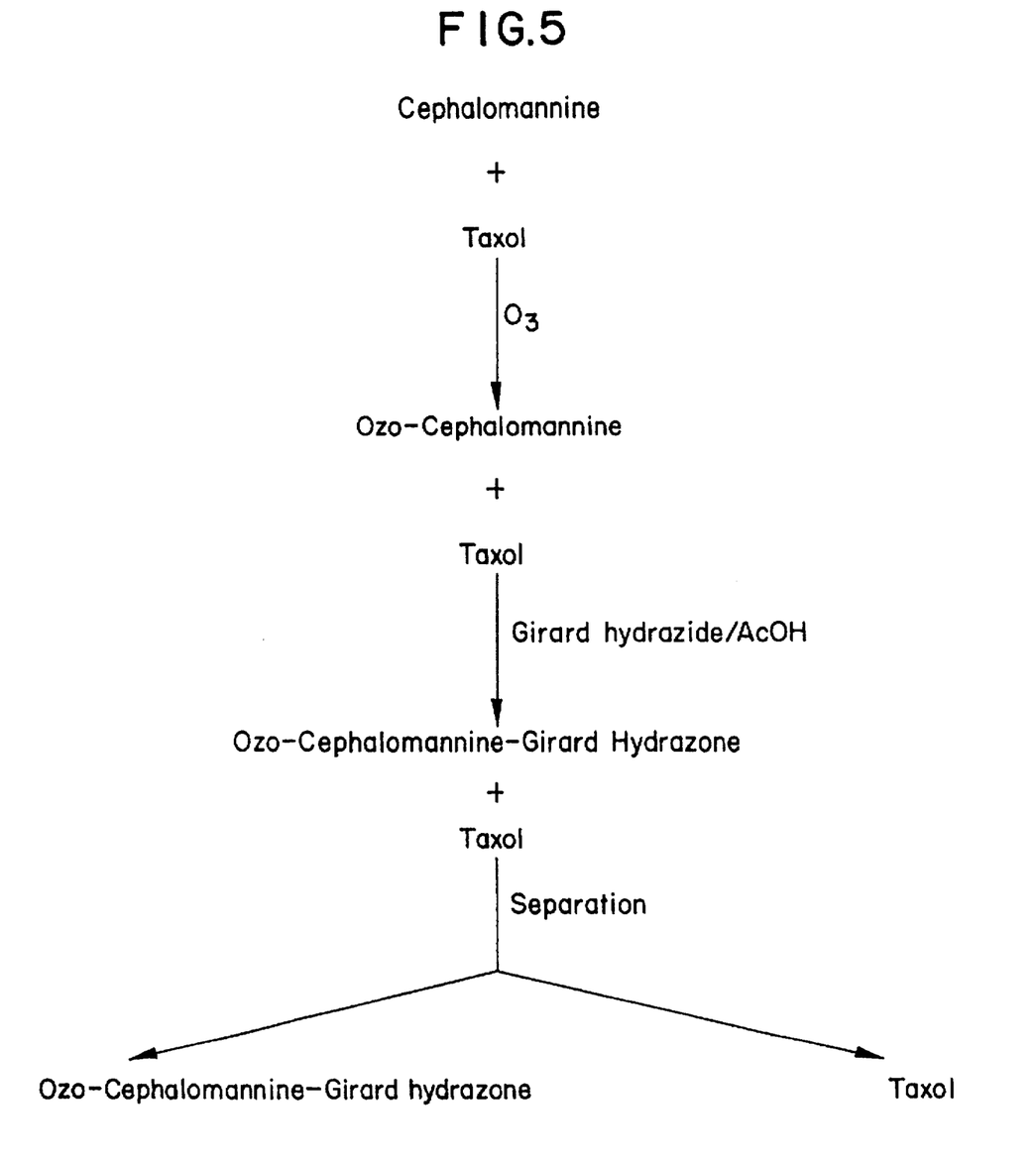
FIG. 5 shows a flow diagram for the separation of taxol and cephalomannine using ozone, followed by treatment with Girard hydrazide and a separation method.

In general the present invention relates to a high yield selective process for the separation of ozone oxidizable compounds from non-oxidizable compounds in unpurified, partially purified, and purified mixtures of biomass extracts as shown in FIG. 1. The preferred embodiment of the present invention is a three step process and is described below using a Taxus brevifolia extract as an example. The first step includes contacting a mixture of taxanes containing cephalomannine and taxol with ozone in stoichiometric quantities, see FIGS. 5 and 8. The second step involves selectively converting the oxidized cephalomannine and other oxidized related compounds to water-soluble hydrazones in the presence of taxol. The third step includes the separation of the water-soluble oxidized taxane hydrazones from taxol and other unreactive compounds by selective precipitation, liquid/liquid extraction or other methods. The three steps of the present invention are summarized in FIG. 5.

As a baseline by which to compare the present invention, the Kingston et al. process discussed previously was run on both high and low purity mixtures of taxanes. The Kingston et al. paper reported that their process had been run on purified and partially purified taxane mixtures that contained cephalomannine and taxol as shown in FIG. 3. However, the partially purified mixture referred to was calculated to be 80% by weight for the taxol plus cephalomannine. No reference was made as to the usefulness of the process disclosed by Kingston et al. for mixtures with purities below the 80% by weight level, such as very impure mixtures that contain less than 1% taxol by weight and less than 1% cephalomannine by weight.

To confirm the usefulness of Kingston's reported process for high purity mixtures of taxanes, the process was repeated using purified cephalomannine (90% cephalomannine by weight, no taxol). The experiment was run on 214 mg of cephalomannine (no taxol) using the Kingston et al. reported method. The isolated product, 114 mg of cephalomannine-diol (57% yield), was characterized by spectroscopic methods and the data matched well with the Kingston et al. reported data. The Kingston et al. process was then performed on a dried, unpurified 505 mg sample of taxanes that contained 0.21% taxol by weight and 0.058% cephalomannine by weight as determined by HPLC. Several portions of excess osmium tetroxide were required to fully oxidize the cephalomannine in the crude mixture. A total of approximately 2000 molar equivalents of osmium tetroxide relative to cephalomannine were added. The reaction required eight days and the resulting crude mixture was very thick and difficult to manipulate. No separation of the oxidized cephalomannine and taxol was possible due to the very difficult manipulation of the mixture.

The Kingston et al. paper also describes a catalytic method for the oxidation of cephalomannine in the presence of taxol. The catalytic method is apparently provided by Kingston et al. as a way to reduce the cost and toxicity problems associated with osmium tetroxide. The catalytic process was repeated using purified cephalomannine (90% by weight, no taxol) to confirm the usefulness of this process for purified mixtures of taxanes. The experiment was performed at 0° C. on 5.9 mg of cephalomannine (90% by weight) in an acetone solvent to yield a mixture that contained the expected diol as determined by HPLC comparison with a standard of the diol that was prepared via the stoichiometric route. The Kingston et al. process was then performed on a dried 1.4 g sample of impure taxanes that contained 0.21% taxol by weight and 0.058% cephalomannine by weight as determined by HPLC. The taxane sample was not completely soluble in the acetone solvent system, even with sonication. Addition of the catalyst system followed by stirring resulted in no decrease in the amount of cephalomannine in the mixture even after several days reaction time.

The present invention is effective for the separation of susceptible taxanes as very pure single compounds or in very pure mixtures. Samples of pure cephalomannine, or a 50:50 mixture of pure taxol and pure cephalomannine work well, for example. In addition, the present invention is also effective for the separation of susceptible taxanes in very crude mixtures of taxanes.

The first step of the process of the present invention is ozone oxidation or ozonolysis of cephalomannine and related compounds in the presence of taxol and other taxanes. Ozone oxidation is effective over a wide range of temperatures including, but not limited to −100° C. to 50° C. and requires only the solution of material, and an ozone generator capable of producing 1 to 10% ozone in an oxygen or air stream. The ozone is bubbled through the liquid mixture of taxanes for the time required, and then the mixture is purged with an inert gas followed by the evaporation of the solvent leaving a dry solid. The liquid mixture is prepared by dissolving a partially pure or impure mixture of taxane into a solvent such as methylene chloride, chloroform, methyl alcohol, acetic acid or mixtures thereof. In the alternative, solvents such as saturated hydrocarbons, halogenated solvents, alcohols, ethers, aldehydes, ketones, organic acids, organic acid derivatives, esters, waters and mixtures thereof may also be used.

Ozone is available, for example, from an ozone generator capable of producing at least 8 grams of ozone an hour or 0.42 pounds/day at no less than 1% weight concentration in clean, dry air (−60° F. dewpoint) when operated with 115 volt, 60 Hertz current and 8 psig pressure; or at least 16 grams of ozone an hour or 0.85 pounds/day at no less than 2% weight concentration in pure, clean, dry oxygen (−60° F. dewpoint) when operated with 115 volt, 60 Hertz current and 8 psig pressure. The concentration of ozone in the oxygen stream can be determine by a variety of methods. Titrametric analysis of an acidic potassium iodide solution after specific treatment times with ozone is a preferred method. The use of sudan red 7B (a dye) has been reported for following ozonolysis reactions. In addition, calibrated ozone meters are available from certain manufacturers. The ozone may also be delivered to the reaction mixture as a solution of ozone in solvent.

Figure 7:
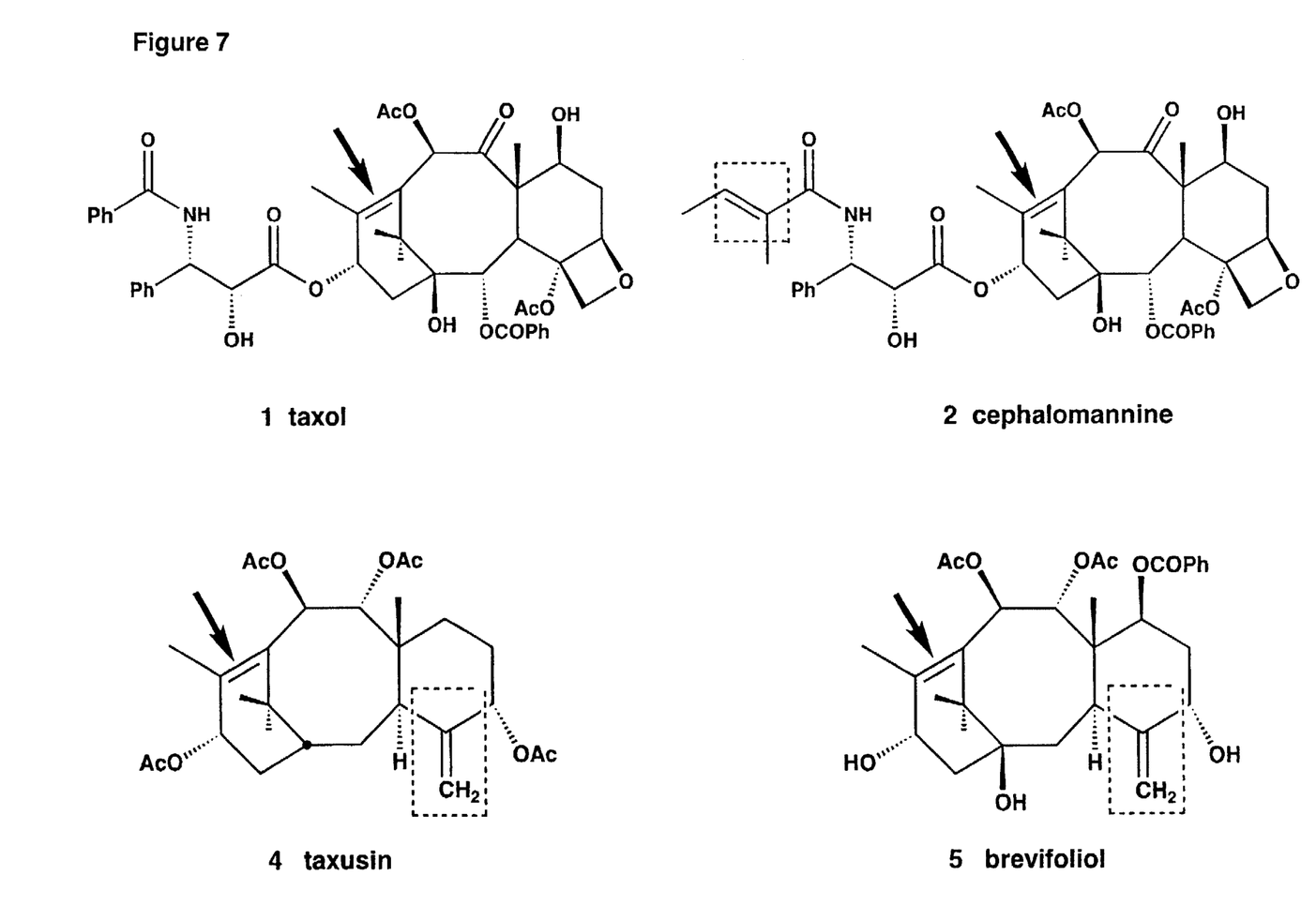
FIG. 7 shows the functional group selectivity of ozone with different taxanes.

The number of molar equivalents of ozone added is dependent upon the purity of the mixture or weight percent of taxol and cephalomannine, and the concentration of cephalomannine and other compounds that react with ozone. Generally, less pure mixtures of taxanes require more molar equivalents, relative to cephalomannine, of ozone to completely oxidize the cephalomannine than do pure mixtures of taxanes. The less pure mixtures of taxanes contain several compounds that compete with the cephalomannine for the available ozone introduced into the mixture. Taxusin 4 and brevifoliol 5, shown in FIG. 7, are two compounds commonly found in *Taxus brevifolia* biomass that will most likely be oxidized along with cephalomannine. The oxidation will occur preferentially at the olefin functional groups outlined by the dotted lines in FIG. 7. The tetrasubstituted olefin indicated by the bold arrow in each of the structures, shown in FIG. 7, is much less reactive than are the less substituted olefins. Under conditions outlined herein, the tetrasubstituted olefin is essentially unchanged during the present oxidation process. Other ozone oxidation susceptible taxanes have functional groups similar to those outline by the dotted lines discussed above. The high selectivity of the ozone oxidation process for specific taxanes in impure and partially pure mixtures is unexpected and can greatly simplify the purification process of taxol as described herein.

The oxidation via ozone of the present invention exhibits many advantages for purification purposes over oxidation methods that employ chemical oxidants such as hydrogen peroxide, perchloric acid, sodium periodate, potassium permangante, sodium hypochlorite, osmium tetroxide and peracetic acid. Oxidation using ozone is more rapid, more selective for cephalomannine in the presence of taxol, more complete for short reaction times (minutes), and less toxic than the other listed oxidants in the process of this invention.

In addition, ozone oxidation is more amenable to the treatment of very crude mixtures of taxol and other unreactive compounds and cephalomannine and related compounds than are other oxidants. Also, very important in the commercial purification of taxol is the fact that ozone can be introduced at an early point in the purification process, whereas this is not possible when using chemical oxidants such as osmium tetroxide.

Furthermore, the use of ozone in an oxidation process with a fairly sensitive natural product such as taxol would not be expected to leave taxol unaffected. This is especially true considering taxol, cephalomannine, taxusin and brevifoliol all have an olefin functional group in the A ring, see the arrows in FIG. 7, which might be expected to react with ozone. In addition, taxol and other taxanes contain many functional groups that are susceptible to oxidation, such as tertiary hydrogen atoms, aryl rings, and ethers. The high yield and the selective ozone oxidation of the tiglate tail portion of the cephalomannine side chain in unpurified, partially purified, and purified mixtures of taxanes under a variety of conditions is a completely unexpected and surprising result.

Figure 8:
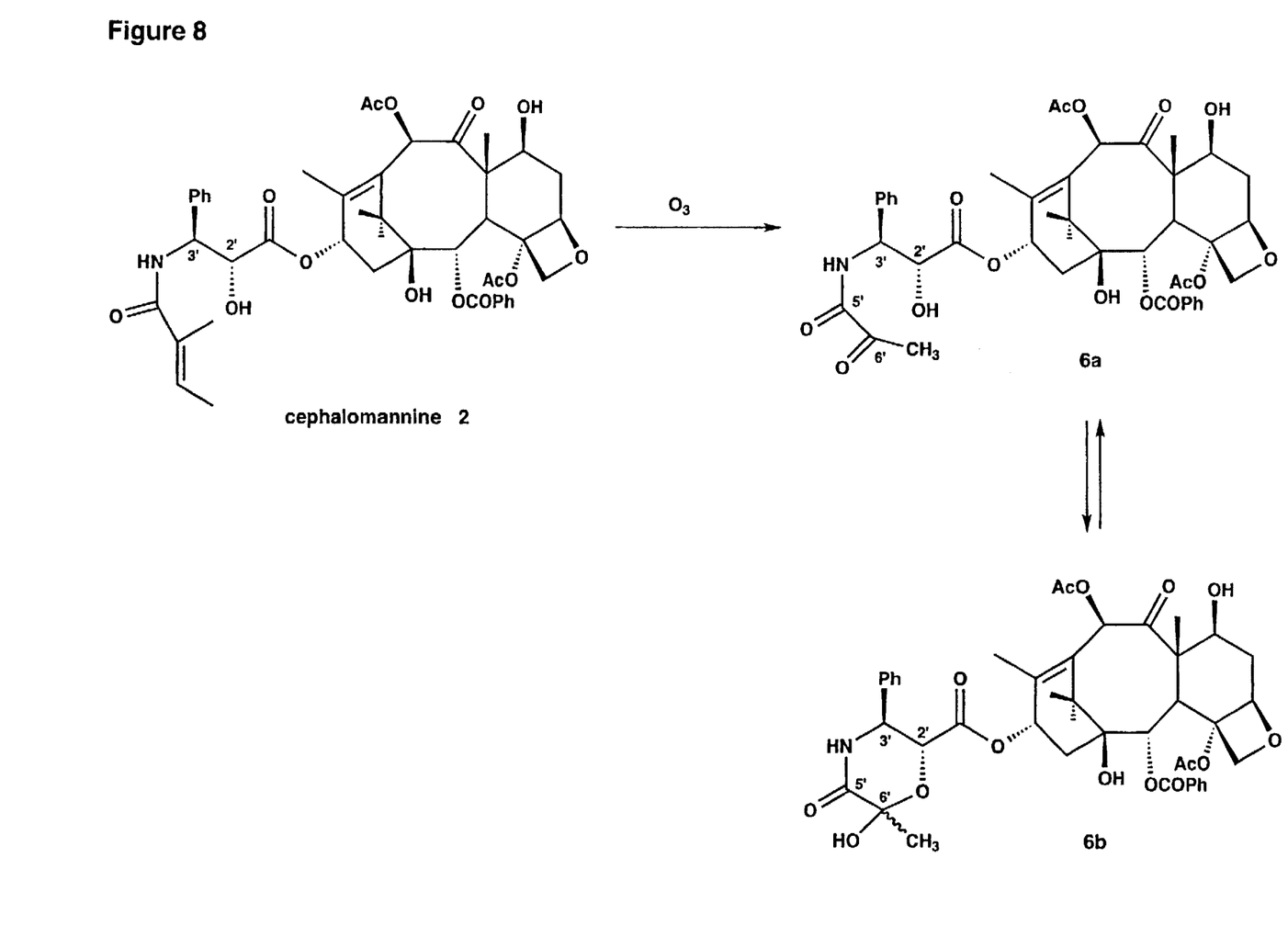
FIG. 8 shows the reaction of cephalomannine and ozone.

An accessible carbonyl group such as a ketone or aldehyde is crucial for the second step in the separation process. As shown in FIG. 8, treatment of a solution of cephalomannine in a solvent, such as methylene chloride, with ozone results in a quantitative yield of the desired compound, discussed above, which exists as the open and closed ring forms hereafter called 6a/6b. The predominant form in non-alcoholic solvents is 6a. The oxidation product of cephalomannine, 6a/6b, has been fully characterized as the α-keto-amide derivative by spectroscopy and other methods.

Figure 10:
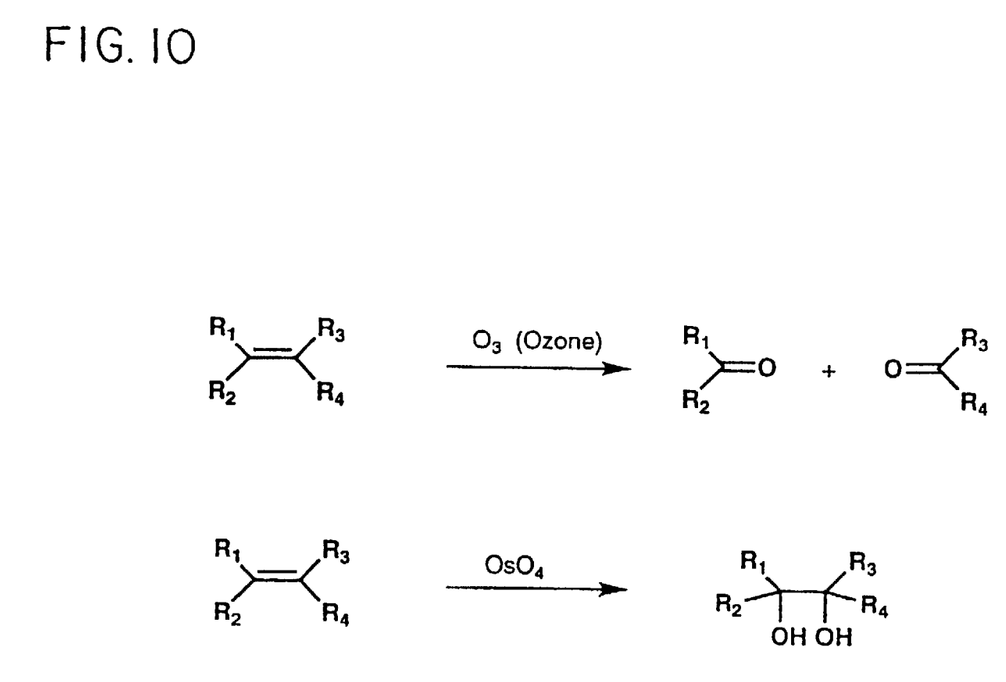
FIG. 10 shows a comparison of chemical oxidation by ozone and osmium tetroxide.

In general, comparison of chemical oxidation by ozone and osmium tetroxide is shown in FIG. 10. Ozone, as used in the present invention, results in the oxidative cleavage of the olefin bond; whereas, osmium tetroxide reported in the Kingston et al. paper discussed previously, results in the dihydroxylation of the olefin bond as opposed to cleavage. A more specific comparison of chemical oxidation of cephalomannine by ozone and osmium tetroxide is illustrated by structures 3 shown in FIG. 3, and 6a/6b shown in FIG. 8, respectively. The diol formed by osmium tetroxide as reported by Kingston et al. is not useful nor is it capable of the formation of a water-soluble Girard hydrazone, the second step in the separation process.

Figure 9:
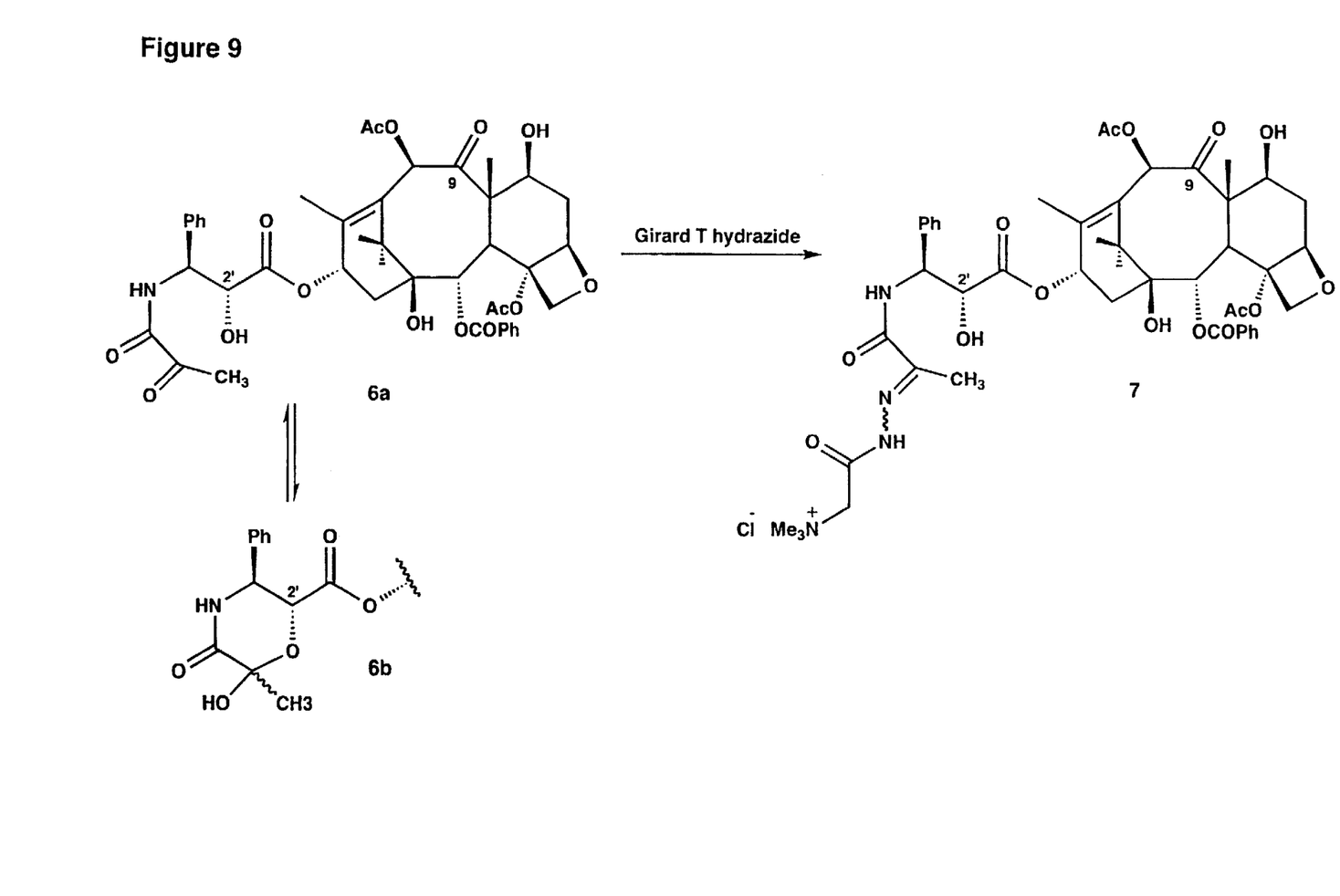
FIG. 9 shows the reaction of oxidized cephalomannine, from ozonolysis, and Girard T hydrazide.

The second step of the process of the present invention is the conversion of the oxidized compounds, resulting from the first step, which contain reactive ketone or aldehyde functional groups including the oxidized cephalomannine, to water-soluble hydrazones. The functional group transformation for oxidized cephalomannine to the hydrazone formation is shown in FIG. 9. A review of the chemistry of this class of compounds has been provided by O. H. Wheeler, "The Girard Reagents" Chemical Reviews 62:205–221 (1962), incorporated herein by reference. The Girard reagents are available from several manufacturers. The oxidized compounds contained in the dried reaction mixture are converted to water-soluble hydrazones. This is accomplished through the addition of a Girard reagent to the dry solids obtained from the step above. The mixture of solids are subsequently dissolved, preferably in acetic acid. However, the hydrazone formation is effective in halogenated solvents, alcohols, ethers, organic acids, esters, water and mixtures thereof.

Figure 6:
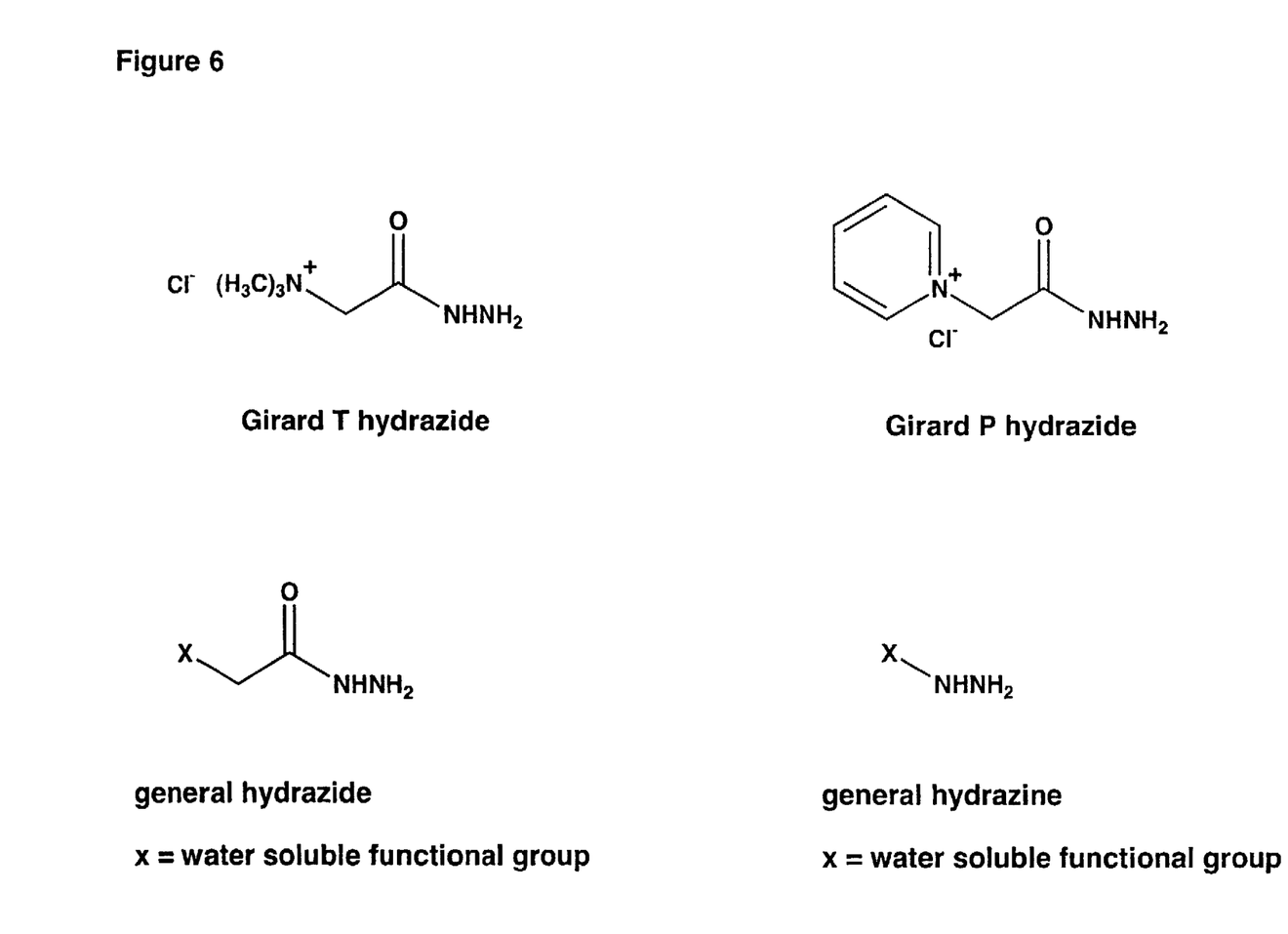
FIG. 6 shows the structure of the Girard T and Girard P reagents.

The appropriate amount of Girard T or P hydrazide used to convert the oxidized taxanes to hydrazones is based on an initial assay for cephalomannine and other similar taxanes in the starting mixture. Similar to the ozone oxidation step less pure mixtures of taxanes require more molar equivalents, relative to cephalomannine, of Girard hydrazide reagent to completely form the hydrazone of the oxidized cephalomannine, than do pure mixtures of taxanes. The hydrazone formation step is similar to the ozone oxidation step in that the conversion of the oxidized taxanes to hydrazones can be followed by HPLC. However, the hydrazones are not mobile in the analytical chromatography method used, see the Example section. Consequently, observation that a peak is missing when comparing chromatograms of the starting oxidized mixture and the hydrazine/hydrazone mixture is a good indication that the conversion of the oxidized compound to the hydrazone is complete. The process of the present invention is not limited in the type of hydrazide or hydrazine that is suitable. The Girard P hydrazide is suitable for this process as well as the Girard T hydrazide. In addition, other water-soluble hydrazines or hydrazides may work as well as the Girard hydrazides for the formation of water-soluble hydrazones of the oxidized cephalomannine. The requirements for the water-soluble hydrazide reagents for the process described herein include: high water solubility of the hydrazide; high reactivity with the pyruvamide ketone group of the oxidized cephalomannine; no reactivity with the C-9 ketone of taxol, shown in FIGS. 2 and 9; high water solubility of the hydrazone(s) of the oxidized cephalomannine and related compounds; and stability of the hydrazone to the formation and manipulation steps for the separation process. In a more broad sense, hydrazide based materials that form hydrazones, that have different solubility than unreactive compounds in the starting material, will also work. Reactive hydrazides bound to polymer supports, for example, should work well. General structures for water-soluble hydrazides and hydrazines that may be useful for the present process are shown in FIG. 6.

The third step of the process of the present invention is the separation of the water-soluble hydrazones of the oxidized cephalomannine and related compounds from taxol and other taxanes based on the differing solubilities and polarities of these materials. Two specific methods are discussed below for the separation of the water-soluble hydrazones from taxol. For very pure mixtures of taxol and the Girard hydrazone of oxidized cephalomannine, selective precipitation or liquid/liquid extraction leads to isolation of taxol with high recovery. These two methods are extremely mild and very inexpensive alternatives to chromatography. For impure mixtures of taxol, the separation works equally well, but larger volumes of solvent and processes such as continuous liquid/liquid extraction may be required for high recovery of taxol.

Solvents effective for the selective precipitation of taxol include solvents generally miscible with water. Useful solvents include but are not limited to alcohols, ethers, aldehydes, ketones, organic acids, esters and mixtures thereof. The preferred solvent system is methanol/water. Solvents effective for the liquid/liquid extraction include solvents generally immiscible with water, yet taxol has a high solubility in these solvents. Useful solvents include but are not limited to saturated and unsaturated hydrocarbons, halogenated solvents, alcohols, ethers, aldehydes, ketones, esters and mixtures thereof The preferred solvent systems are ethyl acetate/water or methylene chloride/water.

In another embodiment of the present invention very impure mixtures of cephalomannine and taxol containing ratios of 0.1 to 1.0 for cephalomannine/taxol, purity of taxol is between 0.1 and 1% by weight, may be purified according to the basic procedure discussed above. However, the process requires longer ozone treatment times and more equivalents of the Girard reagent for effective conversion. For example, dissolution of a mixture of dried biomass extract that contains taxol and cephalomannine in acetic acid, is followed by treatment with ozone, generally more than 50 molar equivalents relative to cephalomannine. The extent of cephalomannine oxidation can be carefully monitored by HPLC analysis of aliquots of the reaction mixture, (see the Examples section). The solution is then purged with an inert gas such as argon or nitrogen. The Girard reagent is added, generally more than 30 molar equivalents relative to the cephalomannine, and the mixture is heated to approximately 50° C. for between one and twenty hours. The acetic acid solvent is then removed under vacuum. The separation of the hydrazones from the rest of the mixture, which contains taxol, can be effected using selective precipitation or liquid/liquid extraction. Normal or reverse phase chromatography may be used if it is advantageous, however, it is not mandatory for this separation process. Other separation processes that take advantage of the differing solubilities and differing polarities of the water-soluble hydrazones versus taxol may also be useful. Liquid/liquid extraction seems to work well for the very impure mixtures. For example, the residue is dissolved in a ternary mixture of ethyl acetate, water, and methanol at a ratio of 10:2:1. The resulting organic and aqueous phases are separated and the organic phase, which contains the taxol, is washed with water to remove residual aqueous impurities. The HPLC assay of the dried residue from the organic phase shows the recovery of taxol is excellent, greater than 93% in all examples, and the purity of the taxol is generally doubled. The mixture can be carried on to further purification. The cephalomannine, however, has been completely removed thus alleviating one of the more difficult and expensive steps in the purification of taxol from extracts of biomass that also contain cephalomannine.

In a third embodiment partially purified mixtures of cephalomannine and taxol, containing ratios of cephalomannine/taxol of 0.05 to 7.35 with purity of taxol or cephalomannine between 1 and 5% by weight, are separated using the process described directly above. The mixture of cephalomannine and taxol, a dry powder with purities ranging from 1% taxol to 99% taxol is dissolved in an organic solvent such as, acetic acid, methyl alcohol or methylene chloride, after which ozone is bubbled through the solution until the cephalomannine is completely oxidized. The reaction can be monitored by HPLC analysis as described in the Examples section. After the oxidation is finished the reaction mixture is purged with argon or nitrogen gas to remove excess ozone. In all cases the cephalomannine and related compounds are oxidized with high recovery of taxol. The mixtures are then treated with the appropriate amount of Girard T or P hydrazide to effectively convert all of the oxidized cephalomannine and other susceptible oxidized taxanes to Girard T or P hydrazones. The separation of the hydrazones and unreacted hydrazide from the rest of the mixture, which contains taxol, can be effected using the methods discussed above.

In the process of this invention, taxol is not significantly degraded by ozone, and the selective oxidation of cephalomannine and related compounds in the presence of taxol and other unreactive compounds using ozone relies upon the functional group differences between cephalomannine along with related compounds and taxol. It is important to note, however, that taxol will degrade to several unidentified compounds by improper exposure to a large excess of ozone or from improper exposure to a slight excess for an extended period. The degradation of taxol by ozone can be avoided if the reaction is monitored carefully by HPLC. The following Examples describe in detail procedures for carrying out the selective ozone oxidation of samples containing ozone oxidizable compounds, such as cephalomannine, taxusin and brevifoliol from non-oxidizable compounds such as taxol.

The overall separation process of this invention exhibits many other advantages over alternative methods that require chromatography. Chromatography, normal or reverse phase, is very expensive when implemented in a commercial process. The equipment required is highly specialized and expensive. The solid phase material is expensive and after use it requires cleaning and/or disposal. Chromatographic processes require eluent fractionation which is time consuming and involves fraction analysis. Solvent systems and solvent recovery are often more complex than with more homogenous solvents and recycle streams such as those from a liquid/liquid extraction process, for example. In general, a process that does not require chromatography is more efficient and consequently less expensive than a process that requires chromatography.

EXAMPLES

The following examples provide specific processes for the selective oxidation of cephalomannine and other susceptible compounds in unpurified, partially purified or purified samples of taxanes. These selective oxidations work equally well for samples that contain ozone susceptible compounds with or without taxol or cephalomannine. The following examples also provide a method for separating the oxidized compounds, specifically oxidized cephalomannine from taxol and other unreactive taxanes. All scientific and technical terms have the meanings as understood by one with ordinary skill in the art. The term "biomass" as used herein includes Taxus species and cell culture of Taxus species. The impure mixtures, that is, crude biomass extracts can be obtained, for example, by methods described in a recent publication (Rao, Koppaka V., "Method for the Isolation and Purification of Taxane Derivatives", International Publication Number, WO 92/07842, May 14, 1992), incorporated herein by reference.

All solvents and reagents employed were used as received from the manufacturer except pyridine which was distilled prior to use. Reactions were monitored by thin-layer chromatography, (TLC), using 0.20 mm E. M. Industries Silica Gel 60 (aluminum support) silica gel plates. Reactions were also monitored by high pressure liquid chromatography, (HPLC). Aliquots of crude reaction mixtures for HPLC analysis were removed from the reaction vessel with a 3 µl micro-pipette and diluted to 200 µl in an HPLC sample vial (with insert). The HPLC system consists of a model L-6200 pump, Model AS-4000 or L-3000 UV/VIS/DAD detector (Hitachi Instruments, Inc.). The system was equipped with an NEC 286 computer with 40M hard drive and Lab Manager HPLC software (Hitachi Instruments, Inc.). HPLC columns used included a 4.6 mm×250 mm column, packed with 5 µm diphenyl material (Supelco, Inc.); a 4.6 mm×250 mm, 5 µm, 60 angstrom pentafluorophenyl (PFP) column (ES Industries); and a 4.6 mm×250 mm phenyl guard column (Jones Chromatography). The ozone generator used was a Polymetrics Laboratory Ozonator T-816. The ozone delivery concentration was 0.0046 mmole/second at settings of 100 volts, 60 Hz current, 3.0 psig pressure and a flow rate of 2 SLMP. The ozone flow was calibrated using the method described by the manufacturer. Silica gel for flash chromatography (230 to 400 mesh) was supplied by Scientific Products. A Bruker WP-270 and ACE-300, Varian Gemini 400, and a JEOL FX90Q Spectrometer were employed for $^1H$ and $^{13}C$ NMR spectra with chemical shifts reported in parts per millison, (ppm), relative to tetramethylsilane using residual non-deuterated NMR solvent for reference. Yields refer to chromatographically pure compounds and are not optimized. Purity of products were judged to be greater than 90% on the basis of spectrophotometric homogeneity unless otherwise stated. Chromatographic purity as used herein refers to the HPLC normalized peak area percentage at 227 nm for a given component. Mass spectra were measured at M-Scan Inc., 137 Brandywine Parkway, West Chester, Pa. 19380, using a VG Analytical 2-SE high field mass spectrometer or a VG platform mass spectrometer using electrospray mode. Spectroscopic analyses were determined using an Analect Diamond-20 FTIR with an XAD-Plus microscope. The instrument was equipped with an ACR Advanced Logic Research 486 computer with 200M hard drive and an Analect FX80 software package.

Example I (Demonstration of Prior Art)

Procedure for oxidation of purified cephalomannine with osmium tetroxide (stoichiometric method).

$OsO_4$ in pyridine (0.020M, 24.5 ml, 2.1 equivalents) was added to a solution of cephalomannine (192 mg, 0.23 mmole) in dry pyridine (12.88 ml, 0.02 M) and mixed for 19 hours at room temperature. The reaction was then quenched with 10% $NaHSO_3$ (43 ml) and mixed for 2.5 hours. The mixture was acidified with 3N HCl to pH 1 (paper) and extracted 3 times with EtOAc. The organic layer was washed twice with brine, dried over $Na_2SO_4$, and evaporated. The light green residue was chromatographed on silica gel (gradient EtOAc/hexane) giving 114 mg (57% yield) of a white solid ($R_f$=0.41, 10:90 $MeOH/CH_2Cl_2$). The spectrometric analyses of the solid match with Kingston's reported values ("Modified Taxols, 7. A Method For The Separation Of Taxol And Cephalomannine", Journal of Natural Products, 55, 259–261, (1992)).

Example II (Demonstration of Prior Art)

Procedure for oxidation of purified cephalomannine with osmium tetroxide (catalytic method).

To 5.9 mg (0.007 mmol) of cephalomannine dissolved in acetone was added tetraethylammonium acetate (0.7 mg, 0.003 mmol, 0.43 equivalents). The mixture was cooled to 0° C. and t-butyl hydroperoxide (1.7 µl, 2.54 equivalents of a 70% $H_2O$ solution) and osmium tetroxide (2.5 µl, 0.029 equivalents of a 0.070 M solution in t-butyl alcohol) were added. The mixture was stirred for one hour at 0° C. and then 1.5 hours at room temperature. A sample was analyzed by HPLC and the reaction appeared to be finished. The HPLC and TLC data indicate a very similar product mixture was formed by the catalytic method as by the stoichiometric method.

Example III

Oxidation of impure cephalomannine/taxol with osmium tetroxide (stoichiometric method).

Dried natural product extract (505.3 mg) containing cephalomannine (0.3 mg, 0.058% by weight) was dissolved in dry pyridine (1.3 ml). To the solution was added in portions $OsO_4$ in pyridine (0.077 M) over a seven day period at room temperature until no cephalomannine remained as shown by HPLC. It took between 1,176 and 1,990 equivalents of $OsO_4$ (5.345 ml and 9.045 ml) to completely oxidize the available cephalomannine.

Example IV

Oxidation of impure cephalomannine/taxol with osmium tetroxide (catalytic method).

A suspension of dried, ground biomass extract (1.40 g) containing 0.81 mg cephalomannine (0.058% by weight) was prepared in acetone (1.5 ml originally), and 3×0.5 ml additional portions were added to facilitate mixing. The initially liquid/granular mixture turned into a liquid/gummy tar within ten minutes even with sonication. The liquid was sampled for HPLC analysis, thus confirming the presence of cephalomannine. Tetraethylammonium acetate (0.08 mg, 0.32 equivalents) was added and the mixture was cooled to 0° C. To this mixture was added t-butyl hydroperoxide (0.3 µl, 2.28 equivalents of a 70% $H_2O$ solution) followed by addition of osmium tetroxide (0.3 µl, 0.025 equivalents of a 0.79 M solution). The mixture was stirred for 1.25 hours at 0° C., and then 2 hours at room temperature. At this point, no oxidation of cephalomannine was observed when a small aliquot was removed from the mixture and analyzed by HPLC. Additional aliquots were removed after 17.75 and 25.75 hours of total reaction time. The HPLC analysis of these samples indicated no decrease in the amount of cephalomannine or increase in the amount of expected diol.

Example V

Procedure for the oxidation of pure cephalomannine with ozone.

Cephalomannine 2 (90% by weight, total weight: 2.702 g; cephalomannine: 2.432 g, 29.24 mmol) in $CH_2Cl_2$ (65 ml, 0.45 M) at −60° to −75° C. was treated with ozone (39.744 mmol, 0.0046 mmol/s, 1.4 equivalents) for 184 minutes. The solution was then purged with argon at room temperature for 5 minutes following evaporation. Analysis by HPLC indicated the reaction was complete, and NMR showed the equilibrium mixture of 6a and 6b. Resonances for the major compound are listed. $^1H$ NMR (90 MHz, $CDCl_3$) 1.11 (s, 3H), 1.21 (s, 3H), 1.29–1.58 (m, 2H), 1.64 (s, 3H), 1.78 (s, 3H), 1.89–2.16 (m, 3H), 2.20 (s, 3H), 2.31 (s, 3H), 2.24 (s, 3H), 2.40–2.72 (m, 1H), 3.75 (d, J=6.8 Hz, 2H), 3.98–4.47 (m, 3H), 4.64 (m, 1H), 4.89 (d, J=8.5 Hz, 1H), 5.13–5.68 (m, 2H), 5.98–6.20 (m, 1H), 6.25 (s, 1H), 7.27–7.73 (m, 8H), 7.85 (d, J=9.4 Hz, 1H), 8.07 (d, J=7.7 Hz, 2H). $^{13}C$ NMR (12 MHz, $CDCl_3$) 9.54, 14.65, 20.76, 21.65, 22.51, 24.37, 26.79, 35.62, 35.62, 43.12, 45.72, 55.00, 58.48, 72.04, 72.04, 73.31, 74.96, 75.58, 76.44, 79.00, 81.16, 84.32, 126.97, 126.97, 128.60, 128.60, 128.60, 128.89, 128.89, 129.16, 130.11, 130.11, 133.24, 133.65, 137.14, 141.68, 159.70, 166.88, 170.30, 171.07, 171.93, 195.94, 203.55. The diagnostic signals in the $^{13}C$ NMR spectrum for the minor isomer in $CDCl_3$ (carbon 6' of the two diastereomers of 6b) are 102.52 and 105.35 ppm. The diagnostic signals in $CD_3OD$ of 6ab, including possible solvent addition ($CD_3OD$) to both 6a and 6b are 97.9 and 197.2 ppm. FTIR (neat, $cm^{-1}$) 981.6 (m), 1025.9 (m), 1070.3 (m), 1108.9 (m), 1178.3 (m), 1241.9 (s), 1373.1 (m), 1724.0 (s), 2900.4 (w), 2940.9 (w), 3064.3 (w), 3413.4(m), 3490.5 (m). The melting point of an analytically pure sample (chrom purity >97%) was 162°–167° C. Mass Spectrum (FAB, glycerol/thioglycerol matrix) m/z 821 $(M+1)^+$.

Example VI

Oxidation of pure cephalomannine/taxol with ozone and separation using Girard T reagent and selective precipitation.

A mixture of pure taxol (100.6 mg, 0.119 mmole) and cephalomannine (100.5 mg, 0.121 mmole) was dissolved in dry methylene chloride. The mixture was cooled to −78° C. in a dry ice/acetone bath and 3 molar equivalents (compared to cephalomannine) of ozone was bubbled into the solution. After purging the solution with argon, the solvent was removed from the mixture. To the dried reaction mixture was added 1.5 molar equivalents (compared to the original molar amount of cephalomannine) of Girard T hydrazide reagent (30.8 mg). To dissolve the solids, enough acetic acid was added (880 microliters) to make a 0.14 M solution. The reaction mixture was heated to 50° C. with stirring for 2 hours. The acetic acid was evaporated and 800 microliters of methanol (8 ml/1 g of solids) was added to dissolve the mixture. The solution was then heated to 50° C., and enough water (200 microliters) was added slowly to make a 25% $H_2O$/MeOH solution. The solution was allowed to cool slowly to room temperature and then it was placed in a freezer overnight. The following morning the solids (taxol) were isolated by vacuum filtration. After drying, the recovery of taxol was 79.6 mg (79.1%). The solids were recrystallized in MeOH/$H_2O$ to yield 68.1 mg (67.7% recovery). The chromatographic purity of the recovered taxol is 97.5%. The m.p. is 198°–201° C.; the m.p. for a taxol standard: 208°–212° C. The $^{13}C$ NMR data for the isolated taxol matched exactly with that of a standard sample.

Example VII

Oxidation of pure cephalomannine/taxol with ozone and separation using Girard T reagent and liquid/liquid extraction.

An equal mixture of pure cephalomannine (19.7 mg, 0.024 mmol) and pure taxol (19.7 mg, 0.023 mmol) were dissolved in 1.2 ml of acetic acid and treated with 2 molar equivalents of ozone (relative to cephalomannine). The reaction mixture was purged with argon and 5 molar equivalents (relative to cephalomannine) of the Girard T reagent (20.1 mg) was added and the solution was heated to 50° C. After heating for 2 hours, the solvent was removed under vacuum. The dried reaction mixture was dissolved in a minimal amount of ethyl acetate and water and the two phases were separated. The organic phase that contains the taxol was washed sequentially with saturated sodium bicarbonate and brine solutions. The total residue (19.1 mg) after evaporation was 95% taxol by chromatographic purity analysis with a 93% overall recovery.

Example VIII

Oxidation of impure cephalomannine/taxol with $O_3$ and separation using Girard T reagent and liquid/liquid extraction.

A crude product extract of *Taxus brevifolia* bark was assayed. The cephalomannine purity was calculated to be 0.14% and the taxol purity was calculated to be 0.38%. The crude product extract (51.22 g) was dissolved in MeOH (120 ml) and acetic acid (40 ml) and was treated with 200 molar equivalents (relative to cephalomannine) of ozone. After the solution was purged with argon, the solvent was removed under vacuum. The dried reaction mixture and 100 molar equivalents (1.65 g, relative to cephalomannine) of the Girard T reagent were dissolved in MeOH (20 ml) and AcOH (140 ml). The solution was heated to 50° C. in an oil bath and was allowed to mix for 7 hours before the solvent was removed under vacuum. The dried reaction mixture was then dissolved in ethyl acetate (500 ml), water (100 ml) and methanol (45 ml). The methanol was added to the solution to aid in the dissolution of the solids. After the two phases were separated, the aqueous phase was washed twice with ethyl acetate to remove any residual organic soluble materials. The combined organic phases containing taxol were washed three times with water to remove residual aqueous phase impurities. HPLC analysis of the dried organic solids showed the taxol purity increased to 0.9%. The recovery was calculated to be 76% with a 68% decrease in the solids. When the product was analyzed by HPLC/MS (electrospray—Fisons VG), cephalomannine and oxidized cephalomannine were not found, indicating complete removal.

Example IX

Separation of Taxusin and Brevifoliol from Taxol.

A mixture of taxusin (25.2 mg, 0.0512 mmol), brevifoliol (24.5 mg, 0.0478 mmol) and taxol (53.3 mg, 0.0625 mmol) was dissolved in 7.1 ml MeOH (0.014 M). Ozone (10 eq) was bubbled through the solution. The number of equivalents (eq) of ozone was calculate to 5 eq for the taxusin and 5 eq for the brevifoliol. The solution was purged with nitrogen and the solvent removed under vacuum. The solids and Girard T reagent (3 eq, 53.6 mg, relative to the oxidized taxusin and oxidized brevifoliol content) were dissolved in AcOH and heated to 50° C. for 2 hours. The solvent was removed under vacuum. The solids were then dissolved in EtOAc and $H_2O$ (a 50/50 mixture). The two phases were separated. The aqueous phase was extracted with EtOAc two times. The combined organic phases were then washed two times with $H_2O$ followed by brine solution. The organic solution was dried over $MgSO_4$, filtered and concentrated to a solid. The solid was analyzed by HPLC method and showed that taxusin and brevifoliol were removed from the mixture. Taxol was shown to have a chromatographic purity of 91%.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

The embodiments of the invention in which an exclusive property or privilege is claimed are defined as follows:

1. A compound of the formula:

Wherein R denotes an acetyl radical or hydroxyl radical.

2. A compound of the formula:

Wherein R denotes an acetyl radical or hydroxyl radical.

3. A compound of the formula:

Wherein X is a substituent that contains a water-soluble functional group; and wherein R denotes an acetyl radical or hydroxy radical.

4. A compound of the formula:

Wherein X is a substituent that contains a water-soluble functional group; and wherein R denotes an acetyl radical or hydroxy radical.

* * * * *